United States Patent
Alanine et al.

(10) Patent No.: US 6,951,875 B2
(45) Date of Patent: Oct. 4, 2005

(54) CONJUGATED AROMATIC COMPOUNDS WITH A PYRIDINE SUBSTITUENT

(75) Inventors: Alexander Alanine, Schlierbach (FR); Bernd Buettelmann, Schopfheim (DE); Marie-Paule Heitz Neidhart, Hagenthal le Bas (FR); Emmanuel Pinard, Linsdorf (FR); Rene Wyler, Zurich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/277,002

(22) Filed: Oct. 21, 2002

(65) Prior Publication Data

US 2003/0144525 A1 Jul. 31, 2003

(30) Foreign Application Priority Data

Oct. 29, 2001 (EP) .............................................. 01125765

(51) Int. Cl.[7] ........................ A61K 31/44; C07D 213/74
(52) U.S. Cl. .................... 514/336; 514/352; 546/281.4; 546/304; 546/311
(58) Field of Search .............................. 546/281.4, 304, 546/311, 280.4, 307, 312, 329, 334; 514/336, 352, 357

(56) References Cited

U.S. PATENT DOCUMENTS

| | | |
|---|---|---|
| 5,648,369 A | 7/1997 | Kadaba |
| 5,869,676 A | 2/1999 | Niu et al. |
| 5,962,472 A | 10/1999 | Bourson et al. |
| 5,972,976 A * | 10/1999 | Hidaka et al. ............... 514/357 |
| 6,265,426 B1 | 7/2001 | Alanine et al. |
| 6,310,213 B1 | 10/2001 | Alanine et al. |

FOREIGN PATENT DOCUMENTS

| | | | |
|---|---|---|---|
| EP | 1088818 | | 4/2001 |
| WO | WO 99/02497 | * | 1/1999 |

OTHER PUBLICATIONS

Database Registry File on STN– RN 33844–47–2, Abstract No. 75:129625 (1971).*
Yasushi Honma et al., *J. Med. Chem.*, vol. 27, pp. 125–128 (*1984*).
Roger Adams et al., *JACS*, vol. 71, pp. 1186–1195 (*1949*).
M. Adamczyk and D. Watt, *J.Org. Chem.*, vol. 49, pp. 4226–4237 (*1984*).
Chenard & Menniti, *Curr. Pharma. Des.*, vol. 9, pp. 381–404 (*1999*).
Kaminski J.J., et al., Journal of Medicinal Chemistry, vol. 32, No. 8, pp. 1686–1700 (1989).
Chuansheng Niu, et al., Tetrahedron, vol. 54, pp. 6311–6318 (1998).
Jun Li, et al., Current Medicinal Chemistry, vol. 8, No. 2, pp. 121–133 (2001).
Takamura, Keiichi, et al., Chemical Abstract XP002231553 & Yakugaku Zasshi, 91(8), pp. 787–794 (1971).
Padmanabhan, S., et al., Bioorganic & Medicinal Chemistry Letters, vol. 11, pp. 501–504 (2001).

* cited by examiner

*Primary Examiner*—Bernard Dentz
(74) *Attorney, Agent, or Firm*—George W. Johnston; Patricia S. Rocha-Tramaloni; Kimberly J. Prior

(57) ABSTRACT

The present invention relates to compounds of formulae

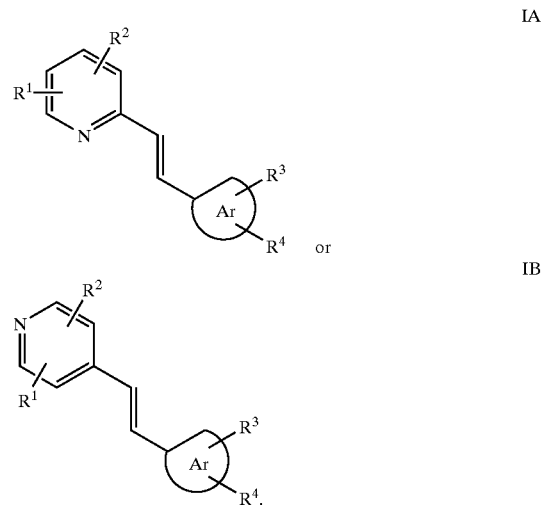

The compounds of the present invention are NMDA (N-methyl-D-aspartate)-receptor subtype blockers and are used in the treatment of diseases related to this receptor.

13 Claims, No Drawings

CONJUGATED AROMATIC COMPOUNDS WITH A PYRIDINE SUBSTITUENT

FIELD OF INVENTION

The present invention is related to compounds of the general formulae

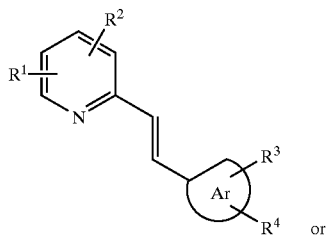
IA

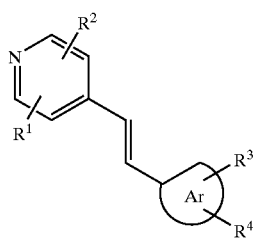
IB

Compounds of formula IA or IB are NMDA(N-methyl-D-aspartate)-receptor subtype selective blockers useful in the treatment or prevention of CNS disorders.

BACKGROUND

Under pathological conditions of acute and chronic forms of neurodegeneration overactivation of NMDA receptors is a key event for triggering neuronal cell death. NMDA receptors are composed of members from two subunit families, namely NR-1 (8 different splice variants) and NR-2 (A to D) originating from different genes. Members from the two subunit families show a distinct distribution in different brain areas. Heteromeric combinations of NR-1 members with different NR-2 subunits result in NMDA receptors displaying different pharmaceutical properties. Possible therapeutic indications for NMDA NR-2B receptor subtype specific blockers include acute forms of neurodegeneration caused, e.g., by stroke and brain trauma, and chronic forms of neurodegeneration such as Alzheimer's disease, Parkinson's disease, Huntington's disease, ALS (amyotrophic lateral sclerosis), neurodegeneration associated with bacterial or viral infections, and, in addition, depression and chronic and acute pain.

SUMMARY

The present invention relates to a compound of formula

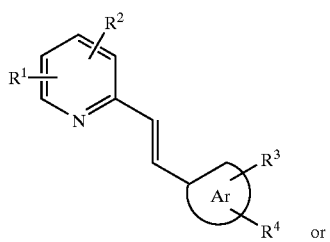
IA

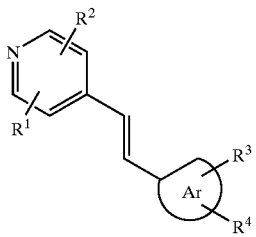
IB wherein $R^1$ and $R^2$ are each independently selected from the group hydrogen, lower alkyl, —$(CH_2)_n NR^5 R^{5'}$ and —$(CH_2)_{n+1}$OH;

$R^5$ and $R^{5'}$ are each independently selected from the group hydrogen and lower alkyl;

$R^3$ and $R^4$ are each independently selected from the group hydrogen, lower alkyl, lower alkoxy, halogen, trifluoromethyl and hydroxy;

Ar is phenyl or thiophenyl;

the dotted line is selected from the group consisting of two hydrogen atoms not forming a bridge and —$CH_2$—$CHR'$—, wherein R' is H or lower alkyl; and n is 0, 1 or 2;

or a pharmaceutically acceptable acid addition salt thereof, with the proviso that when Ar is unsubstituted phenyl and $R^2$ is H, $R^1$ is not 2-amino.

6-styryl-pyridin-2-yl-amine has been specifically described in *J. Med. Chem.*, 1984, 27, 125 for use as antiallergic agent and in *JACS*, 1949, 71, 1186 as an intermediate in a condension reaction of N-substituted pyridones.

Compounds of formulae IA and IB of the present invention may have the following sub-structures:

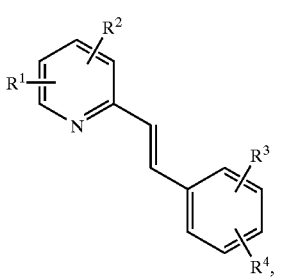
IA-1

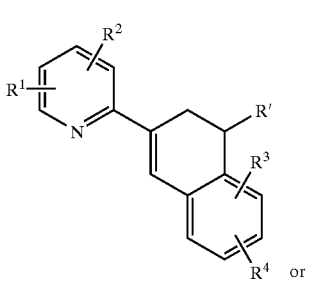
IA-2

-continued

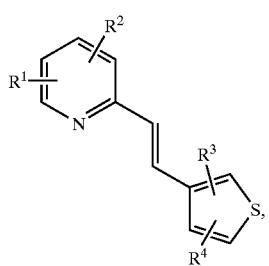
IA-3

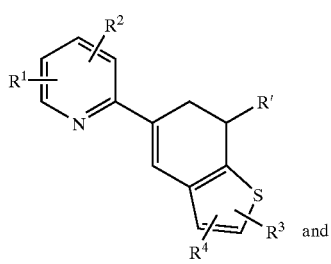
IA-4 and

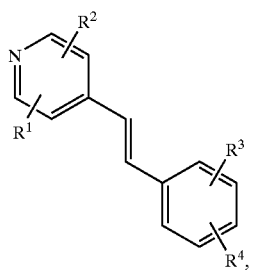
IB-1

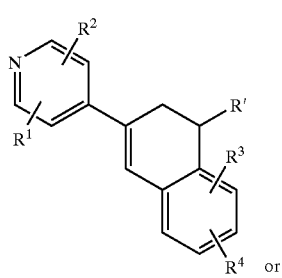
IB-2 or

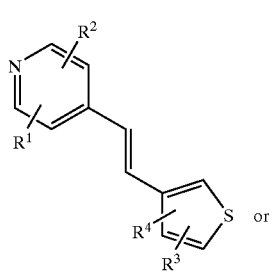
IB-3 or

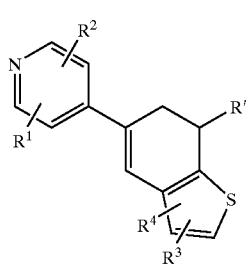
IB-4

$R^1$, $R^2$, $R^3$, $R^4$ and R' are as described above.

The compounds of formulae IA or IB or pharmaceutically acceptable salts thereof are distinguished by valuable therapeutic properties. Compounds of the present invention are NMDA(N-methyl-D-aspartate)-receptor subtype selective blockers, which have a key function in modulating neuronal activity and plasticity which makes them key players in mediating processes underlying development of CNS as well as learning and memory formation.

The present invention relates to compounds of formulae IA and IB or harmaceutically acceptable acid addition salts thereof and the preparation of the compounds of formulae IA and IB or pharmaceutically acceptable salts thereof. The invention also relates to pharmaceutical compositions containing a compound of formulae IA, IB, a combination thereof or a pharmaceutically acceptable acid addition salt thereof and a pharmaceutically acceptable vehicle and the manufacture of such pharmaceutical compositions. The present invention additionly relates to a method of treatment of acute forms of neurodegeneration caused, e.g., by stroke and brain trauma, and chronic forms of neurodegeneration such as Alzheimer's disease, Parkinson's disease, Huntington's disease, ALS (amyotrophic lateral sclerosis), neurodegeneration associated with bacterial or viral infections, and, in addition, depression and chronic and acute pain comprising administering to a patient in need of such treatment a therapeutically effective amount of a compound of formulae Ia, Ib or combinations thereof or a pharmaceutically acceptable salt thereof.

DETAILED DESCRIPTION

The following definitions of the general terms used in the present description apply irrespective of whether the terms in question appear alone or in combination.

As used herein, the term "lower alkyl" denotes a straight- or branched-chain alkyl group containing from 1 to 7 carbon atoms, for example, methyl, ethyl, propyl, isopropyl, butyl and the like. Preferred lower alkyl groups contain from 1 to 4 carbon atoms.

The term "halogen" denotes chlorine, iodine, fluorine and bromine.

The term "lower alkoxy" denotes a group wherein the alkyl residue is as defined above and the alkyl group is connected via an oxygen atom.

The term "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Preferred compounds of formula IA-1, for example the following compounds are selected from the group:
trans-4-methyl-6-styryl-pyridin-2-yl-amine,
trans-2-styryl-pyridin-4-yl-amine and
trans-C-(6-styryl-pyridin-2-yl)-methylamine.

Further preferred are compounds of formula IA-2, wherein R' is hydrogen, for example compounds selected from the group:
2-(3,4-dihydro-naphthalen-2-yl)-pyridin-4-yl-amine,
2-(3,4-dihydro-naphthalen-2-yl)-(6-methyl-pyridin-4-yl-amine,
[4-amino-6-(3,4-dihydro-naphthalen-2-yl)-pyridin-2-yl]-methanol,
2-(3,4-dihydro-naphthalen-2-yl)-5-methyl-pyridin-4-yl-amine,
2-(3,4-dihydro-naphthalen-2-yl)-(6-methyl-pyridin-4-yl-amine,

[2-(3,4-dihydro-naphthalen-2-yl)-pyridin-4-yl]-methyl-amine,
C-[6-(3,4-dihydro-naphthalen-2-yl)-pyridin-2-yl]-methylamine,
2-(7-chloro-3,4-dihydro-naphthalen-2-yl)-pyridin-4-yl-amine,
2-(5,7-dimethyl-3,4-dihydro-naphthalen-2-yl)-pyridin-4-yl-amine,
2-(7-chloro-3,4-dihydro-naphthalen-2-yl)-6-methyl-pyridin-4-yl-amine,
2-(7-chloro-3,4-dihydro-naphthalen-2-yl)-6-methyl-pyridin-4-yl-amine and
2-(7-chloro-3,4-dihydro-naphthalen-2-yl)-5-methyl-pyridin-4-yl-amine.

Additional preferred compounds of formula IA-2 are further those, wherein R' is methyl, for example the compounds selected from the group:
rac.-2-(4-methyl-3,4-dihydro-naphthalen-2-yl)-pyridin-4-yl-amine,
rac.-2-methyl-6-(4-methyl-3,4-dihydro-naphthalen-2-yl)-pyridin-4-yl-amine and
rac.-5-methyl-2-(4-methyl-3,4-dihydro-naphthalen-2-yl)-pyridin-4-yl-amine.

Preferred compounds of formula IA-4 are those, wherein R' is hydrogen, for example the compounds selected from the group
2-(6,7-dihydro-benzo[b]thiophen-5-yl)-pyridin-4-yl-amine and
2-(6,7-dihydro-benzo[b]thiophen-5-yl)-5-methyl-pyridin-4-yl-amine.

A preferred compound of formula IB-1 is, for example, the following compound:
trans-6-methyl-4-styryl-pyridin-2-yl-amine.

A further preferred group of compounds of formulae IA and IB are those, wherein one of $R^1$ or $R^2$ is amino.

The above-mentioned compounds of formulae IA and IB can be prepared in accordance with the invention by
reacting a compound of formula

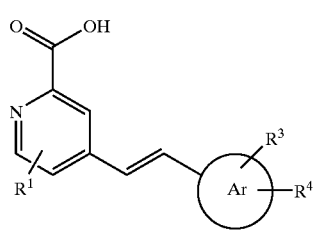

IIA with diphenyl phosphoryl azide forming a compound of formula

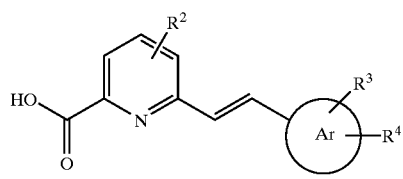

IA-1a reacting the amino group of a compound of formula IA-1a with a compound of formula $R^5X$ to give a compound of formula

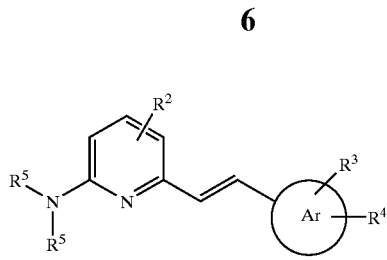

IA-1b wherein $R^2$–$R^4$ and Ar have the significances given above, $R^5$ is lower alkyl and X is halogen, or reacting a compound of formula

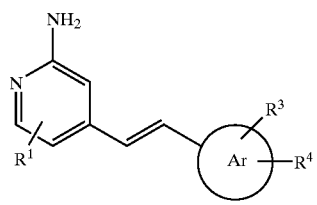

IIB with diphenyl phosphoryl azide to a compound of formula

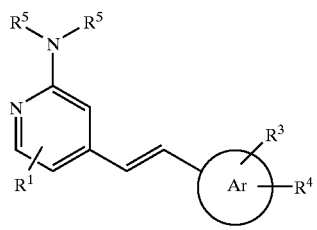

IIB-1a wherein $R^2$–$R^4$ and Ar have the significances given above, or reacting the amino group of a compound of formula IB-1a with a compound of formula $R^5X$ to give a compound of formula

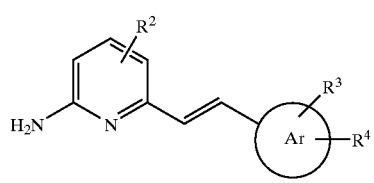

IIB-1b wherein $R^1$, $R^3$ and $R^4$ and Ar have the significances given above, $R^5$ is lower alkyl and X is halogen, or reacting a compound of formula

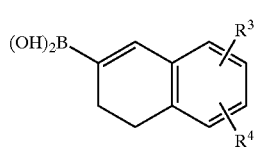

X with a compound of formula

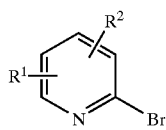

XIA to a compound of formula

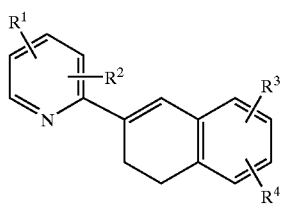

IA-2 wherein $R^1$ to $R^4$ have the significances given above, or reacting a compound of formula

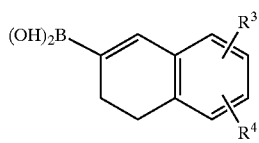

X with a compound of formula

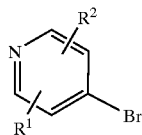

XIB () a compound of formula

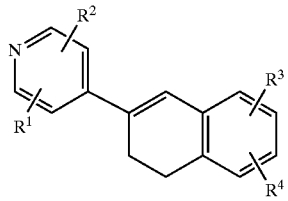

IB-2 wherein $R^1$ to $R^4$ have the significances given above, or if desired, converting the compound of formula I obtained into a pharmaceutically acceptable salt.

In the following the preparation of compounds of formulae IA and IB are described in more detail:

In accordance with the process variants, described above, and with schemes 1–3, described below, compounds of formulae IA and IB may be prepared by known procedures, for example the following:

In accordance with schemes 1 and 2 a compound of formula IVA or IVB may be prepared as follows:

To a refluxing solution of 2-picoline-1-oxide or 4-picoline-1-oxide and potassium tert.-butanolate in butanol is added portionwise an aldehyde of formula VA. Reflux is maintained for about 90 min. Then the mixture is cooled, diluted and extracted. The combined organic phases are dried and concentrated to provide a compound of formulae IVA or IVB. The obtained compound is then reacted first with dimethylsulfate and then with NaCN. After extraction and crystallization a compound of formulae IIIA or IIIB is obtained, for example 6-(2-p-tolyl-vinyl)-pyridine-2-carbonitrile (IIIA) or trans-6-methyl-4-styryl-pyridine-2-carbonitrile (IIIB). The corresponding carbonitrile compounds and HCl are further refluxed for 3 hr. All volatiles are distilled off and the residue is stirred with $H_2O$, filtered and dried to obtain a compound of formulae IIA or IIB. The most preferred compounds of formulae IA-1a or IB-1a, wherein one of $R^1$ or $R^2$ is amino, may then be prepared as follows: A compound of formula IIA or IIB is brought to reaction with triethylamine, diphenyl phosphoryl aside and butanol. After extractive workup the residue is refluxed about 4 hr with HCl and after a further workup a compound of formula IA-1a or IB-1a is obtained. The amino group may then further modified by alkylation to obtain compounds of formulae IA-1b or IB-1b.

In accordance with scheme 3, a compound of formula IA-2 or IB-2 is obtained as follows: A compound of formula IX, for example 3-bromo-1,2-dihydro-naphthalene, is prepared in analogy to M. Adamczyk and D. S. Watt, *J. Org. Chem.*, 1984, 49, 422.6. This compound is then solved in diethylether, cooled in a dry ice bath and tert.-butyllithium solution in pentane is added. The solution is stirred about for 30 min, then triisopropylborate is added. The reaction mixture is brought to rt and treated with HCl. After 15 min the organic phase is dried, evaporated and precipitated with pentane to provide a compound of formula X.

This compound is further treated with a compound of formula XIA or XIB as follows: A solution of a compound of formula XIA or XIB and palladium tetrakis (triphenylphosphine) in toluene is stirred at room temperature (rt) for about 15 min. Then a compound of formula X and an aqueous $K_2CO_3$ solution is added and the resulting mixture is refluxed for about 30 min. Toluene is added and the organic phase is dried and concentrated to obtain a compound of formula IA-2 or IB-2.

Pharmaceutically acceptable salts can be manufactured according to methods which are known in the art. The acid addition salts of compounds of formulae IA and IB are especially well suited for pharmaceutical use.

In the following schemes 1–3 are described processes for preparation of compounds of formulae IA and IB, starting from known compounds, from commercial products or from compounds, which can be prepared in conventional manner.

The preparation of compounds of formulae IA and IB are described in more detail in working examples 1–41

Scheme 1

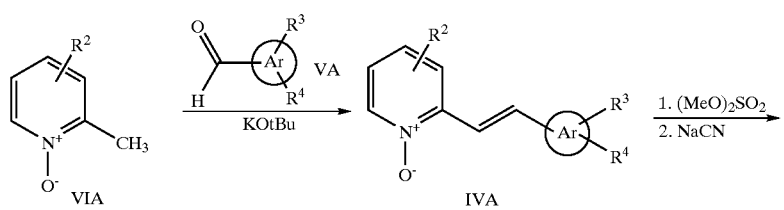

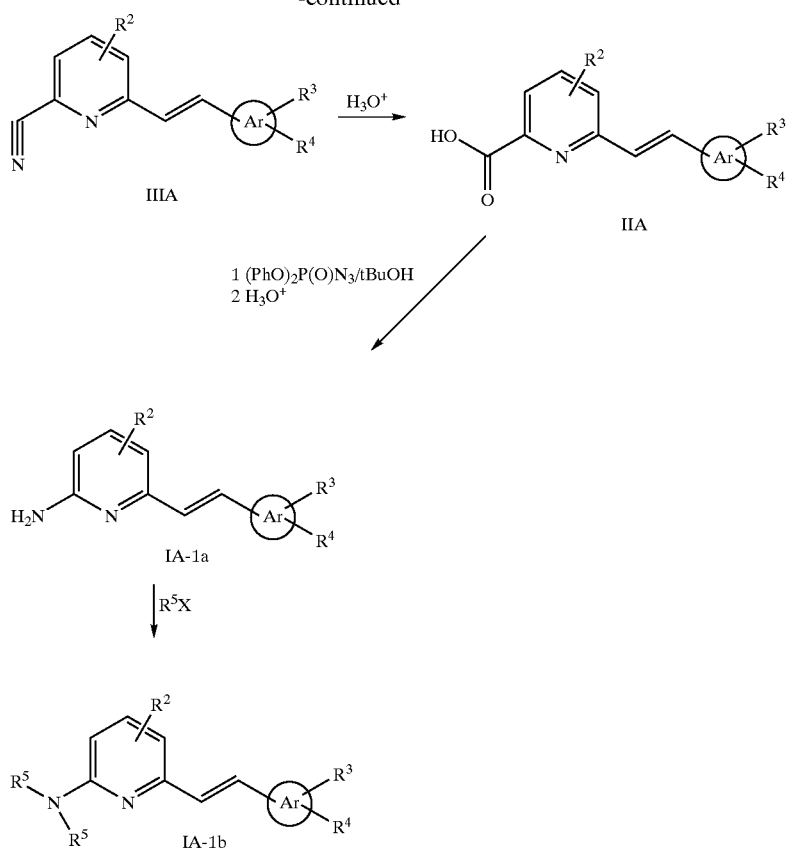
The substituents $R^1$ to $R^4$ and Ar are described above and THF is tetrahydrofuran.
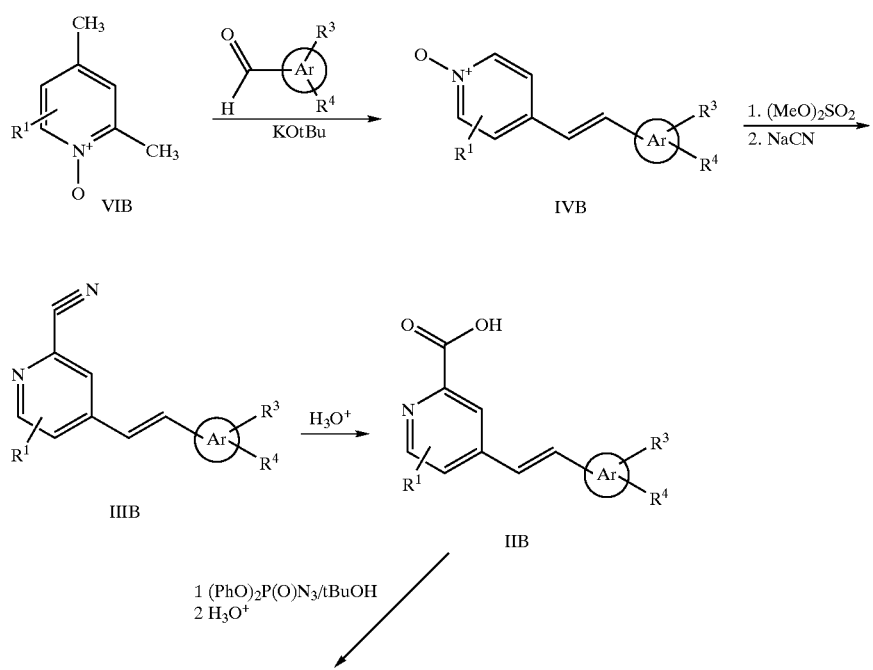

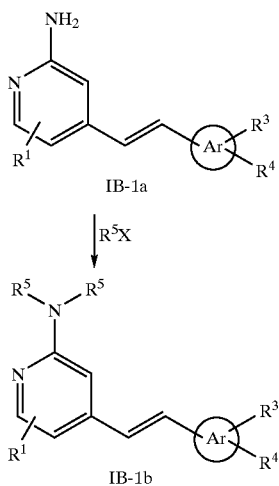

IB-1a

↓ R⁵X

IB-1b

The substituents $R^1$, $R^3$ and $R^4$ and Ar are described above.

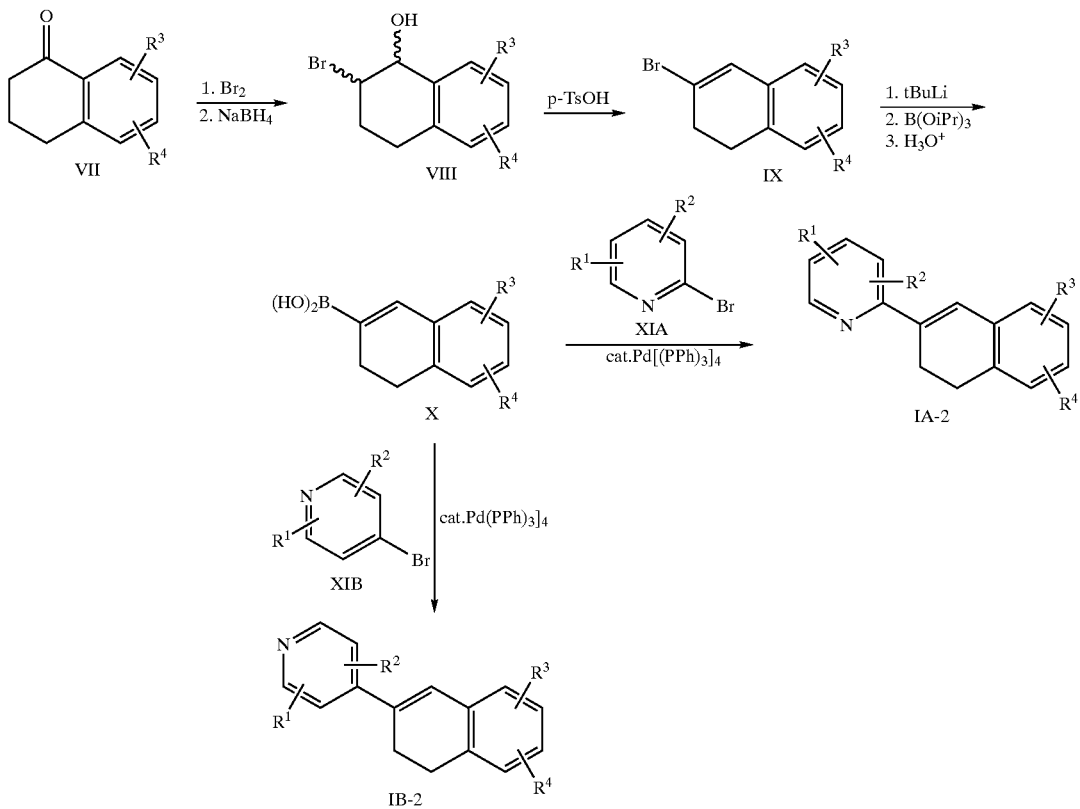

Scheme 3

The substituents $R^1$, $R^2$, $R^3$ and $R^4$ and Ar are described above.

As mentioned earlier, the compounds of formulae IA and IB or their pharmaceutically acceptable acid addition salts possess valuable pharmacodynamic properties. They are NMDA-receptor subtype 2B selective blockers, which have a key function in modulating neuronal activity and plasticity which makes them key players in mediating processes underlying development of CNS as well as learning and memory formation.

The compounds were investigated in accordance with the test given hereinafter.

Test Method

³Ro 25-6981 binding (Ro 25-6981 is [R—(R*,S*)]-α-(4-Hydroxy-phenyl)-β-methyl-4-(phenyl-methyl)-1-piperidine propanol)

Male Fullinsdorf albino rats weighing, between 150–200 g were used. Membranes were prepared by homogenization of the whole brain minus cerebellum and medulla oblongata with a Polytron (10,000 rpm, 30 seconds), in 25 volumes of a cold Tris-HCl 50 mM, EDTA 10 mM, pH 7.1 buffer. The homogenate was centrifuged at 48,000 g for 10 minutes at 4° C. The pellet was resuspended using the Polytron in the same volume of buffer and the homogenate was incubated at 37° C. for 10 minutes. After centrifugation the pellet was homogenized in the same buffer and frozen at −80° C. for at least 16 hours but not more than 10 days. For the binding assay the homogenate was thawed at 37° C., centrifuged and the pellet was washed three times as above in a Tris-HCl 5 mM, pH 7.4 cold buffer. The final pellet was resuspended in the same buffer and used at a final concentration of 200 mg of protein/ml.

$^3$H-Ro 25-6981 binding experiments were performed using a Tris-HCl 50 mM, pH 7.4 buffer. For displacement experiments 5 nM of$^3$H-Ro 25-6981 were used and non specific binding was measured using 10 mM of tetrahydroisoquinoline and usually it accounts for 10% of the total. The incubation time was 2 hours at 4° C. and the assay was stopped by filtration on Whatmann GF/B glass fiber filters (Unifilter-96, Packard, Zürich, Switzerland). The filters were washed 5 times with cold buffer. The radioactivity on the filter was counted on a Packard Top-count microplate scintillation counter after addition of 40 mL of microscint 40 (Canberra Packard S. A., Zürich, Switzerland).

The above procedure was performed to determine data for calculation of an $IC_{50}$ value. The $IC_{50}$ value is a concentration expressed in micromoles ($\mu$M) for a test compound at which 50% of the ligand (in this determination, $^3$H-Ro 25-6981) bonded to the receptor is displaced. The binding ability of the compounds of the invention was measured in vitro using a minimum of 10 concentrations and repeated at least once. The specific binding at each concentration was then calculated as the % of the maximum specific binding (100%) obtained in the same experiment, in the absence of a test compound. Competitive displacement of $^3$H-Ro 25-6981 was observed, with complete displacement of the radioligand from specific binding sites (usually about 0% of specific binding at the highest concentrations tested). An $IC_{50}$ value was then calculated with all the ten datapoints (% of specific bound) by plotting the data on a semilogarithmic scale with a sigmoidal fit (Log of the molar concentration on X-axis vs. % of specific bound on the Y-axis) using Microsoft Excel fit software or Microcal Origin software. The pooled normalized values were analyzed using a non-linear regression calculation program which provide $IC_{50}$ with their relative upper and lower 95% confidence limits.

The $IC_{50}$ ($\mu$M) of preferred compounds of formulae IA or IB, tested in accordance with the above mentioned methods, is <0.1 $\mu$M. In table I below representative $IC_{50}$ values are described.

TABLE I

| Example No. | $IC_{50}$ ($\mu$M) |
|---|---|
| 14 | 0.01 |
| 16 | 0.04 |
| 18 | 0.08 |
| 19 | 0.018 |
| 22 | 0.032 |
| 24 | 0.011 |
| 26 | 0.038 |
| 27 | 0.052 |
| 28 | 0.038 |

TABLE I-continued

| Example No. | $IC_{50}$ ($\mu$M) |
|---|---|
| 30 | 0.02 |
| 34 | 0.057 |
| 36 | 0.023 |
| 37 | 0.082 |
| 13 | 0.03 |

The compounds of formulae IA, IB or combinations thereof and their salts, as herein described, can be incorporated into standard pharmaceutical dosage forms, for example, for oral or parenteral application with the usual pharmaceutical adjuvant materials, for example, organic or inorganic inert carrier materials, such as, water, gelatin, lactose, starch, magnesium stearate, talc, vegetable oils, gums, polyalkylene-glycols and the like. The pharmaceutical preparations can be employed in a solid form, for example, as tablets, suppositories, capsules, or in liquid form, for example, as solutions, suspensions or emulsions. Pharmaceutical adjuvant materials can be added and include preservatives stabilizers, wetting or emulsifying agents, salts to change the osmotic pressure or to act as buffers. The pharmaceutical preparations can also contain other therapeutically active substances.

The dosage can vary within wide limits and will, of course, be fitted to the individual requirements in each particular case. In the case of oral administration the dosage lies in the range of about 0.1 mg per dosage to about 1000 mg per day of a compound of general formula I although the upper limit can also be exceeded when this is shown to be indicated.

The following examples illustrate the present invention in more detail. However, they are not intended to limit its scope in any manner. All temperatures are given in degree Celsius.

EXAMPLE 1

6-Styryl-pyridin-2-ylamine hydrochloride

Prepared according to the literature: Y. Honma et al., J. Med. Chem., 1984, 27, 125.

EXAMPLE 2

6-(2-p-Tolyl-vinyl)-pyridin-2-yl-amine hydrochloride a) 2-(2-p-Tolyl-vinyl)-pyridine 1-oxide To a refluxing solution of 2-picoline-1-oxide (10.9 g, 100 mmol), potassium tert.-butanolate (11.2 g, 100 mmol) in butanol (100 ml) was added portion-wise p-tolualdehyde (12.0 g, 100 mmol). Reflux was maintained for 90 min. Then the mixture was cooled to rt, diluted with $H_2O$ (100 ml) and extracted with $CH_2Cl_2$. The combined organic phases were dried with $MgSO_4$, concentrated and chromatographed ($SiO_2$ with $CH_2Cl_2$/MeOH=95:5) to provide the title compound (11.6 g, 55%) as a yellow solid material. MS: m/e=211 (M$^+$).

b) 6-(2-p-Tolyl-vinyl)-pyridine-2-carbonitrile

In a variation to the procedure referred to in example 1, 2-(2-p-tolyl-vinyl)-pyridine 1-oxide (9.8 g, 46 mmol) was reacted first with dimethylsulfate (5.8 g, 46 mmol) and then with NaCN (2.74 g, 56 mmol). After extraction and crystallization 6-(2-p-tolyl-vinyl)-pyridine-2-carbonitrile (5.8 g, 57%) was obtained as a yellow crystalline material. Mp. 137–138° C. (isopropanol), MS: m/e=220 (M$^+$)

c) 6-(2-p-Tolyl-vinyl)-pyridine-2-carboxylic acid

In a variation to the procedure referred to in example 1, 6-(2-p-tolyl-vinyl)-pyridine-2-carbonitrile (3.0 g, 14 mmol) and 37%) HCl (70 ml) was refluxed for 3 hr. All volatiles were distilled off and the residue stirred with $H_2O$ (100 ml), filtered and dried over NaOH to obtain the title compound (2.81 g, 84%) as a yellow crystalline material. MS: m/e=239 ($M^+$).

d) 6-(2-p-Tolyl-vinyl)-pyridin-2-yl-amine 1:1 hydrochloride

In a variation to the procedure referred to in example 1, 6-(2-p-tolyl-vinyl)-pyridine-2-carboxylic acid (2.81 g, 11.7 mmol) was brought to reaction with triethylamine (1.21 g, 12.0 mmol), diphenyl phosphoryl azide (3.56 g, 12.9 mmol) and butanol (33 ml). After extractive workup the residue was refluxed (4 hr) with 3N HCl. Extractive workup and chromatography ($SiO_2$ with $AcOEt/hexane/NEt_3$=10:20:1) afforded the title compound as an oil which was crystallized as the yellow hydrochloride salt (0.95 g, 33%). Mp.>250° C. ($MeOH/Et_2O$), MS: m/e=210 ($M^+$).

EXAMPLE 3

6-[2-(4-Methoxy-phenyl)-vinyl]-pyridin-2-yl-amine hydrochloride a) 2-[2-(4-Methoxy-phenyl) -vinyl]-pyridine 1-oxide Following the general method described in example 2a, 2-picoline-1-oxide was reacted with potassium tert.-butanolate and p-anisaldehyde. After extraction and chromatography the title compound was obtained as a yellow solid material. MS: m/e=227 ($M^+$).

b) 6-[2-(4-Methoxy-phenyl)-vinyl]-pyridine-2-carbonitrile

Following the general method described in example 2b, 2-[2-(4-methoxy-phenyl)-vinyl]-pyridine 1-oxide was reacted first with dimethylsulfate and then with NaCN. After extraction and crystallization the title compound was obtained as a yellow crystalline material. Mp. 121–122° C. (isopropanol), MS: m/e=236 ($M^+$)

c) 6-[2-(4-Methoxy-phenyl)-vinyl]-pyridine-2-carboxylic acid

Following the general method described in example 2c, 6-[2-(4-methoxy-phenyl)-vinyl]-pyridine-2-carbonitrile was hydrolyzed with 37% HCl. After workup the title compound was isolated as a yellow crystalline material. MS: m/e=255 ($M^+$).

d) 6-[2-(4-Methoxy-phenyl)-vinyl]-pyridin-2-yl-amine 1:1 hydrochloride

Following the general method described in example 2d, the title compound was obtained as a yellow crystalline material by reaction of 6-[2-(4-methoxy-phenyl)-vinyl]-pyridine 2-carboxylic acid with triethylamine, diphenyl phosphoryl azide and butanol followed by hydrolysis with HCl. Mp. 224–226° C. ($MeOH/Et_2O$), MS: m/e=226 ($M^+$).

EXAMPLE 4

6-[2-(4-Chloro-phenyl)-vinyl]-pyridin-2-yl-amine hydrochloride a) 2-[2-(4-Chloro-phenyl)-vinyl]-pyridine 1-oxide Following the general method described in example 2a, 2-picoline-1-oxide was reacted with potassium tert.-butanolate and 4-chloro-benzaldehyde. After extraction and chromatography the title compound was obtained as a yellow solid material. MS: m/e=231 ($M^+$).

b) 6-[2-(4-Chloro-phenyl)-vinyl]-pyridine-2-carbonitrile

Following the general method described in example 2b, 2-[2-(4-chloro-phenyl)-vinyl]-pyridine 1-oxide was reacted first with dimethylsulfate and then with NaCN. After extraction and crystallization the title compound was obtained as a beige crystalline material. Mp. 113–115° C.(isopropanol), MS: m/e=240 ($M^+$).

c) 6-[2-(4-Chloro-phenyl)-vinyl]-pyridine-2-carboxylic acid

Following the general method described in example 2c, 6-[2-(4-chloro-phenyl)-vinyl]-pyridine-2-carbonitrile was hydrolyzed with 37%) HCl. After workup the title compound was isolated as a yellow crystalline material. MS: m/e=259 ($M^+$).

d) 6-[2-(4-Chloro-phenyl)-vinyl]-pyridin-2-yl-amine 1:1 hydrochloride

Following the general method described in example 2d, the title compound was obtained as a yellow crystalline material by reaction of 6-[2-(4-chloro-phenyl)-vinyl]-pyridine 2-carboxylic acid with triethylamine, diphenyl phosphoryl azide and butanol followed by hydrolysis with HCl. Mp.>250° C. ($MeOH/Et_2O$), MS: m/e=231 ($M^+$).

EXAMPLE 5

6-[2-(3,4-Dichloro-phenyl)-vinyl]-pyridin-2-yl-amine hydrochloride a) 2-[2-(3,4-Dichloro-phenyl)-vinyl]-pyridine 1-oxide Following the general method described in example 2a, 2-picoline-1-oxide was reacted with potassium tert.-butanolate and 3,4-dichloro-benzaldehyde. After extraction and chromatography the title compound was obtained as a yellow solid material. MS: m/e=265 ($M^+$).

b) 6-[2-(3,4-Dichloro-phenyl)-vinyl]-pyridine-2-carbonitrile

Following the general method described in example 2b, 2-[2-(3,4-dichloro-phenyl)-vinyl]-pyridine 1-oxide was reacted first with dimethylsulfate and then with NaCN. After extraction and crystallization the title compound was obtained as a white crystalline material. Mp. 124–125° C. (hexane), MS: m/e=274 ($M^+$).

c) 6-[2-(3,4-Dichloro-phenyl)-vinyl]-pyridine-2-carboxylic acid

Following the general method described in example 2c, 6-[2-(3,4-dichloro-phenyl)-vinyl]-pyridine-2-carbonitrile was hydrolyzed with 37% HCl. After workup the title compound was isolated as a yellow crystalline material. MS: m/e=293 ($M^+$).

d) 6-[2-(3,4-Dichloro-phenyl)-vinyl]-pyridin-2-yl-amine 1:1 hydrochloride

Following the general method described in example 2d, the title compound was obtained as a yellow crystalline material by reaction of 6-[2-(3,4-dichloro-phenyl)-vinyl]-pyridine 2-carboxylic acid with triethylamine, diphenyl phosphoryl azide and butanol followed by hydrolysis with HCl. Mp.>250° C. (EtOH), MS: m/e=265 ($M+H^+$).

EXAMPLE 6

6-[2-(4-Fluoro-phenyl)-vinyl]-pyridin-2-yl-amine hydrochloride a) 2-[2-(4-Fluoro-phenyl)-vinyl]-pyridine 1-oxide Following, the general method described in example 2a, 2-picoline-1-oxide was reacted with potassium tert.-butanolate and 4-fluoro-benzaldehyde. After extraction and chromatography the title compound was obtained as a yellow solid material. MS: m/e=215 ($M^+$).

b) 6-[2-(4-Fluoro-phenyl)-vinyl]-pyridine-2-carbonitrile

Following the general method described in example 2b, 2-[2-(4-fluoro-phenyl)-vinyl]-pyridine 1-oxide was reacted first with dimethylsulfate and then with NaCN. After extraction and crystallization the title compound was obtained as a yellow crystalline material. MS: m/e=224 ($M^+$).

c) 6-[2-(4-Fluoro-phenyl)-vinyl]-pyridine-2-carboxylic acid

Following the general method described in example 2c, 6-[2-(4-fluoro-phenyl)-vinyl]-pyridine-2-carbonitrile was hydrolyzed with 37% HCl. After workup the title compound was isolated as a yellow crystalline material. MS: m/e=243 (M$^+$).

d) 6-[2-(4-Fluoro-phenyl)-vinyl]-pyridin-2-yl-amine 1:1 hydrochloride

Following the general method described in example 2d, the title compound was obtained as a yellow crystalline material by reaction of 6-[2-(4-fluoro-phenyl)-vinyl]-pyridine 2-carboxylic acid with triethylamine, diphenyl phosphoryl azide and butanol followed by hydrolysis with HCl. Mp.>250° C. (MeOH/Et$_2$O), MS: m/e=214 (M$^+$).

EXAMPLE 7

6-[2-(3-Chloro-phenyl)-vinyl]-pyridin-2-yl-amine hydrochloride a) 2-[2-(3-Chloro-phenyl)-vinyl]-pyridine 1-oxide Following the general method described in example 2a, 2-picoline-1-oxide was reacted with potassium tert.-butanolate and 3-chloro-benzaldehyde. After extraction and chromatography the title compound was obtained as a yellow solid material. MS: m/e=231 (M$^+$).

b) 6-[2-(3-Chloro-phenyl)-vinyl]-pyridine-2-carbonitrile

Following the general method described in example 2b, 2-[2-(4-fluoro-phenyl)-vinyl]-pyridine 1-oxide was reacted first with dimethylsulfate and then with NaCN. After extraction and crystallization the title compound was obtained as a yellow crystalline material which was directly used for the next step.

c) 6-[2-(3-Chloro-phenyl)-vinyl]-pyridine-2-carboxylic acid

Following the general method described in example 2c, 6-[2-(3-chloro-phenyl)-vinyl]-pyridine-2-carbonitrile was hydrolyzed with 37% HCl. After workup the title compound was isolated as a yellow crystalline material. MS: m/e=259 (M$^+$).

d) 6-[2-(3-Chloro-phenyl)-vinyl]-pyridin-2-yl-amine 1:1 hydrochloride

Following the general method described in example 2d, the title compound was obtained as a yellow crystalline material by reaction of 6-[2-(3-chloro-phenyl)-vinyl]-pyridine 2-carboxylic acid with triethylamine, diphenyl phosphoryl azide and butanol followed by hydrolysis with HCl. Mp. 248–249° C. (MeOH/Et$_2$O), MS: m/e=230 (M$^+$).

EXAMPLE 8

6-[2-(2-Fluoro-phenyl)-vinyl]-pyridin-2-yl-amine hydrochloride a) 2-[2-(2-Fluoro-phenyl)-vinyl]-pyridine 1-oxide Following the general method described in example 2a, 2-picoline-1-oxide was reacted with potassium tert.-butanolate and 2-fluoro-benzaldehyde. After extraction and chromatography the title compound was obtained as a yellow solid material. MS: m/e=215 (M$^+$).

b) 6-[2-(2-Fluoro-phenyl)-vinyl]-pyridine-2-carbonitrile

Following the general method described in example 2b, 2-[2-(2-fluoro-phenyl)-vinyl]-pyridine 1-oxide was reacted first with dimethylsulfate and then with NaCN. After extraction and crystallisation the title compound was obtained as a brown crystalline material. MS: m/e=224 (M$^+$).

c) 6-[2-(2-Fluoro-phenyl)-vinyl]-pyridine-2-carboxylic acid

Following the general method described in example 2c, 6-[2-(2-fluoro-phenyl)-vinyl]-pyridine-2-carbonitrile was hydrolyzed with 37% HCl. After workup the title compound was isolated as a yellow crystalline material which was directly used in the next step.

d) 6-[2-(2-Fluoro-phenyl)-vinyl]-pyridin-2-yl-amine 1:1 hydrochloride

Following the general method described in example 2d, the title compound was obtained as a yellow crystalline material by reaction of 6-[2-(2-fluoro-phenyl)-vinyl]-pyridine 2-carboxylic acid with triethylamine, diphenyl phosphoryl azide and butanol followed by hydrolysis with HCl. Mp.>250° C. (MeOH/Et$_2$O), MS: m/e=214 (M$^+$).

EXAMPLE 9

6-[2-(3-Trifluoromethyl-phenyl)-vinyl]-pyridin-2-yl-amine hydrochloride a) 2-[2-(3-Trifluoromethyl-phenyl)-vinyl]-pyridine 1-oxide Following the general method described in example 2a, 2-picoline-1-oxide was reacted with potassium tert.-butanolate and 3-trifluoromethyl-phenyl. After extraction and chromatography the title compound was obtained as a yellow solid material. MS: m/e=265 (M$^+$).

b) 6-[2-(3-Trifluoromethyl-phenyl)-vinyl]-pyridine-2-carbonitrile

Following the general method described in example 2b, 2-[2-(3-trifluoromethyl-phenyl)-vinyl]-pyridine 1-oxide was reacted first with dimethylsulfate and then with NaCN. After extraction and chromatography (SiO$_2$ with CH$_2$Cl$_2$/MeOH= 97/3) the title compound was obtained as a yellow oil and directly used in the next step.

c) 6-[2-(3-Trifluoromethyl-phenyl)-vinyl]-pyridine-2-carboxylic acid

Following the general method described in example 2c, 6-[2-(2-fluoro-phenyl)-vinyl]-pyridine-2-carbonitrile was hydrolyzed with 25% HCl. After workup the title compound was isolated as a yellow crystalline material. MS: m/e=293 (M$^+$).

d) 6-[2-(3-Trifluoromethyl-phenyl)-vinyl]-pyridin-2-yl-amine 1:1 hydrochloride

Following the general method described in example 2d, the title compound was obtained as a yellow crystalline material by reaction of 6-[2-(3-trifluoromethyl-phenyl)-vinyl]-pyridine 2-carboxylic acid with triethylamine, diphenyl phosphoryl azide and butanol followed by hydrolysis with HCl. Mp. 222–223° C. (iPrOH), MS: m/e=264 (M$^+$).

EXAMPLE 10

6-[2-(3-Fluoro-phenyl)-vinyl]-pyridin-2-yl-amine hydrochloride a) 2-[2-(3-Fluoro-phenyl)-vinyl]-pyridine 1-oxide Following, the general method described in example 2a, 2-picoline-1-oxide was reacted with potassium tert.-butanolate and 3-fluoro-benzaldehyde. After extraction and chromatography the title compound was obtained as a yellow solid material. MS: m/e=215 (M$^+$).

b) 6-[2-(3-Fluoro-phenyl)-vinyl]-pyridine-2-carbonitrile

Following the general method described in example 2b, 2-[2-(3-fluoro-phenyl)-vinyl]-pyridine 1-oxide was reacted first with dimethylsulfate and then with NaCN. After extraction and crystallization the title compound was obtained as a beige crystalline material. Mp. 111–112° C. (iPrOH), MS: m/e=224 (M$^+$).

c) 6-[2-(3-Fluoro-phenyl)-vinyl]-pyridine-2-carboxylic acid

Following the genera method described in example 2c, 6-[2-(3-fluoro-phenyl)-vinyl]-pyridine-2-carbonitrile was hydrolyzed with 37% HCl. After workup the title compound was isolated as a yellow crystalline material which was directly used in the next step.

d) 6-[2-(3-Fluoro-phenyl)-vinyl]-pyridin-2-yl-amine 1:1 hydrochloride

Following the general method described in example 2d, the title compound was obtained as a light yellow crystalline material by reaction of 6-[2-(3-fluoro-phenyl)-vinyl]-pyridine 2-carboxylic acid with triethylamine, diphenyl phosphoryl azide and butanol followed by hydrolysis with HCl. Mp.>250° C. (MeOH/Et$_2$O), MS: m/e=214 (M$^+$).

EXAMPLE 11

4-[2-(6-Amino-pyridin-2-yl)-vinyl]-phenol

A suspension of 6-[2-(4-methoxy-phenyl)-vinyl]-pyridine-2-yl-amine (1.0 g, 3.8 mmol) (example 3) in CH$_2$Cl$_2$ (60 ml) was treated with boron tribromide (2.4 ml, 25 mmol) and stirred for 72 hr. The precipitate was filtered, dissolved in AcOEt and washed with aqueous NaHCO$_3$ solution. The organic phase was dried (Na$_2$SO$_4$), concentrated and the residue was chromatographed (SiO$_2$ with CH$_2$Cl$_2$/MeOH/NH$_4$OH=140/10/1) and crystallized to provide 0.20 g (25%) of the light yellow title compound. Mp. 224–225° C. (iPr$_2$O), MS: m/e=213 (M+H$^+$).

EXAMPLE 12 trans-4-Styryl-pyridin-2-yl-amine

Prepared according to the literature: R. Adams, A. W. Schrecker, JACS, 1949, 71, 1186

EXAMPLE 13 trans-6-Methyl-4-styryl-pyridin-2-yl-amine
a) trans-2-Methyl-4-styryl-pyridine 1-oxide Following the general method described in example 2a, 2,4-dimethylpyridine 1-oxide was reacted with potassium tert.-butanolate and benzaldehyde. After extraction and chromatography (SiO$_2$ with CH$_2$Cl$_2$/MeOH=97/3) the title compound was obtained as a yellow solid material (yield 7%)). NMR (250 MHz, DMSO): 2.37 (s, 3H, CH$_3$), 7.20 (d, J=16.5 Hz, 1H, CH=C$\underline{H}$), 7.25–7.75 (m, 8H, arom-$\underline{H}$, C$\underline{H}$=CH), 8.22 (d, J=6.8 Hz, 1H, arom-$\underline{H}$).
b) trans-6-Methyl-4-styryl-pyridine-2-carbonitrile Following, the general method described in example 2b, 2-methyl-4-styryl-pyridine 1-oxide was reacted first with dimethylsulfate and then with NaCN. After extraction and chromatography (SiO$_2$ with CH$_2$Cl$_2$) the title compound was obtained as a yellow crystalline material. MS: m/e=220 (M$^+$).
c) trans-6-Methyl-4-styryl-pyridin-2-carboxylic acid Following the general method described in example 2c, 6-methyl-4-styryl-pyridine-2-carbonitrile was hydrolyzed with 25% HCl. After workup the title compound was isolated as a yellow crystalline material which was directly used in the next step.
d) trans-6-Methyl-4-styryl-pyridin-2-yl-amine Following the general method described in example 2d, the title compound was obtained as a yellow crystalline material by reaction of 6-methyl-4-styryl-pyridine-2-carboxylic acid with triethylamine, diphenyl phosphoryl azide and butanol followed by hydrolysis with HCl. Mp. 149–150° C. (iPr$_2$O), MS: m/e=210 (M$^+$).

EXAMPLE 14 trans-4-Methyl-6-styryl-pyridin-2-yl-amine hydrochloride

In analogy to example 2a-d, the title compound was obtained as a yellow crystalline material by reaction of 4-methyl-2-styryl-pyridine 1-oxide (A. Silhankova et al., Collect. Czech. Chem. Commun., 1989, 54, 1687) with dimethylsulfate followed by NaCN, hydrolysis with HCl followed by treatment with triethylamine, diphenyl phosphoryl azide and butanol followed by hydrolysis with HCl. Mp.>250° C. (EtOH), MS: m/e =210 (M$^+$).

EXAMPLE 15 trans-6-Styryl-pyridin-3-yl-amine

Under inert atmosphere (Ar) a mixture of palladium(II)-acetate (0.45 g, 2 mmol) and triphenylphosphine (0.95 g, 3.6 mmol) in DMF (50 ml) was stirred for 0.5 hr at rt. Then 2-chloro-5-nitropyridine (3.2 g, 20 mmol) and tributyl-styryl-stannane (15.7 g, 40 mmol) was added and the mixture was stirred at 130° C. for 15 hr. The solvent was evaporated and the residue partitioned between AcOEt and 1N HCl. The aqueous phase was neutralized with 6N NaOH and extracted with AcOEt. The organic phase was dried with Na$_2$SO$_4$, concentrated and chromatographed (SiO2 with CH$_2$Cl$_2$/CH$_3$OH=97/3) to (give the title compound (0.90 g, 23%) as a yellow solid. Mp. 159–160° C. (AcOEt), MS: 196 (M$^+$).

EXAMPLE 16 trans-2-Styryl-pyridin-4-yl-amine

Under inert atmosphere (Ar) a mixture of palladium-(II)-acetate (0.117 mg, 0.5 mmol) and triphenylphosphine (0.248 g, 0.9 mmol) in DMF (13 ml) was stirred for 30 min at rt. 2-Bromo-pyridin-4-ylamine (0.90 g, 5.2 mmol) (H. J. den Hertog, C. R. Kolder and W. P. Combe, Rec. Trav. Chim., 1951, 70, 591) was added followed by tributyl-styryl-stannane (3.93 g, 10 mmol). After heating at 130° C. for 15 min the solvent was evaporated and the residue partitioned between AcOEt and 3N HCl. The aqueous phase was neutralized with 6N NaOH and extracted with AcOEt. The organic phase was dried with Na$_2$SO$_4$, concentrated and chromatographed (SiO$_2$ with CH$_2$Cl$_2$/CH$_3$OH/NH$_4$OH= 140/10/1) to give the title compound (0.40 g, 39%) as a colorless solid. Mp. 164–165° C. (AcOEt), MS: 196 (M$^+$).

EXAMPLE 17 trans-Methyl-(6-styryl-pyridin-2-yl)-amine hydrochloride

A solution of 6-styryl-pyridin-2-ylamine (1.0 g, 4.3 mmol) (cf. example 1) in methanol (40 ml) was treated at rt with aqueous formaldehyde (0.33 ml of an 40% of solution, 4.3 mmol) and sodium cyanoborohydride (0.27 g, 4.3 mmol). After 1 hr all volatiles were evaporated and the residue was dissolved in AcOEt. The organic phase was successively washed with saturated aqueous NaHCO$_3$, H$_2$O, saturated aqueous citric acid and water, then dried (Na$_2$SO$_4$), concentrated and chromatographed (SiO2 with AcOEt/hexane/NEt$_2$=10/10/1). The free base of the title compound was obtained as a slightly yellow oil (0.18 g, 20% and crystallized as the yellow hydrochloride. Mp. 157–158° C. (MeOH/Et$_2$O), MS: m/e=210 (M$^+$).

EXAMPLE 18 trans-C-(6-Styryl-pyridin-2-yl)-methylamine hydrochloride

A solution of 6-styryl-pyridin-2-carbonitrile (0.94 g, 4.5 mmol) (cf. example 1) in THF (20 ml) was cooled to 0° C.

After dropwise addition of diisobutylaluminiumhydride (8.0 ml of a 1.2 M solution in toluene) the resulting mixture was stirred at 0° C. for 1 hr and then quenched with saturated Seignette-salt solution. After extraction with AcOEt the combined organic phases were dried over $Na_2SO_4$, concentrated and chromatographed ($SiO_2$ with $CH_2Cl_2/CH_3OH/NH_4OH=140/10/1$) to give the free base of the title compound as a yellow oil (0.16 g, 17%) which was crystallized as a beige hydrochloride salt. Mp. 170° C. (dec.) (MeOH/$Et_2O$), MS: m/e=210 ($M^+$).

EXAMPLE 19

2-(3,4-Dihydro-naphthalen-2-yl)-pyridin-4-yl-amine hydrochloride a) 4-Dihydro-naphthalene-2-boronic acid A solution of 3-bromo-1,2-dihydro-naphthalene (7.7 g, 37 mmol) (M. Adamczyk and D. S. Watt, J. Org. Chem., 1984, 49, 4226) in diethylether (370 ml) was cooled in a dry ice bath and tert.-butyllithium solution (50 ml of a 1.5 M solution in pentane) was added maintaining T<−65° C. At this temperature stirring was continued for 30 min, then triisopropylborate (17.3 ml, 75 mmol) was added. The reaction mixture was brought to rt and treated with 3N HCl (100 ml). After 15 min the organic phase was dried ($Na_2SO_4$), evaporated and precipitated with pentane to provide the title compound (3.83 g) 60%) as a white solid material. MS: m/e=173 ($M-H^-$).

b) 2-(3,4-Dihydro-naphthalen-2-yl)-pyridin-4-yl-amine 1:1 hydrochloride

A solution of 2-bromo-pyridin-4-yl-amine (0.87 g, 5 mmol) and palladium tetrakis(triphenylphosphine) (0.58 g,0.5 mmol) in toluene (25 ml) was stirred at rt for 15 min. Then, 3,4-dihydro-naphthalene-2-boronic acid (0.88 g, 5 mmol) and aqueous 2M $K_2CO_3$ solution (5 ml) was added and the resulting mixture refluxed for 30 min. Toluene (50 ml) was added and the organic phase was dried ($Na_2SO_4$), concentrated and chromatographed ($SiO_2$ with ($CH_2Cl_2/CH_3OH/NH_4OH=300/10/1$) to give the free base of the title compound (0.72 g, 65% ) as a colorless foam. Treatment with hydrogen chloride gave white crystals, Mp. 231–232° C. (EtOH/$Et_2O$), MS: m/e=222 ($M^+$).

EXAMPLE 20

6-(3,4-Dihydro-naphthalen-2-yl)-pyridin-2-yl-amine fumarate

Following the general method described in example 19b, the title compound, was obtained as a light yellow crystalline material by reaction of 6-bromo-pyridin-2-ylamine with palladium tetrakis(triphenylphosphine), 3,4-dihydro-naphthalene-2-boronic acid (example 19a) and 2M $K_2CO_3$ and crystallization of the free base as the fumarate salt. Mp. 153–154° C. (MeOH), MS: m/e=223 ($M+H^+$).

EXAMPLE 21

6-(3,4-Dihydro-naphthalen-2-yl)-4-methyl-pyridin-2-yl-amine fumarate

Following the general method described in example 19b, the title compound was obtained as a light yellow crystalline material by reaction of 6-bromo-4-methyl-pyridin-2-ylamine (A. Kleeman, D. Munro, B. Patel, Eur. Pat. 572093, Dec. 01, 1993) with palladium tetrakis(triphenylphosphine), 3,4-dihydro-naphthalene-2-boronic acid (example 19a) and aqueous 2M $K_2CO_3$ and crystallization of the free base as the fumarate salt. Mp. 142–143° C. (MeOH), MS: m/e=237 ($M+H^+$).

EXAMPLE 22

2- (3,4-Dihydro-naphthalen-2-yl)-6-methyl-pyridin-4-yl-amine fumarate

Following the general method described in example 19b, the title compound was obtained as a white crystalline material by reaction of 2-bromo-6-methyl-pyridin-4-ylamine (A. Puszko, Pr. Nauk. Akad. Ekon. im. Oskara Langego Wroclawiu, 1984, 278, 169) with palladium tetrakis(triphenylphosphine), 3,4-dihydro-naphthalene-2-boronic acid (example 19a) and aqueous 2M $K_2CO_3$ and crystallization of the free base as the fumarate salt. Mp. 202–203° C. (MeOH/$Et_2O$), MS: m/e=236 ($M^+$).

EXAMPLE 23

[4-Amino-6-(3,4-dihydro-naphthalen-2-yl)-pyridin-2-yl]-methanol fumarate a) 6-Bromo-4-nitro-pyridine-2-carboxylic acid To a solution of 2-bromo-6-methyl-4-nitro-pyridine (17.8 g, 82.0 mmol) (A. Puszko, Pr. Nauk. Akad. Ekon. im. Oskara Langego Wroclawiu, 1984, 278, 169) in conc. $H_2SO_4$ (100 ml) $CrO_3$ (32.8 g, 328 mmol) was added maintaining T<55° C. After 4 hr the mixture was heated to 70° C. for 30 min and then cooled to rt. Ice-cold water (500 ml) was added maintaining T<70° C. The mixture was left overnight. The title compound crystallized as a beige material (76%). Mp. 173–175° C. ($H_2O$), MS: m/e=246 ($M^+$).

b) (4-Amino-6-bromo-pyridin-2-yl)-methanol

A solution of 6-bromo-4-nitro-pyridine-2-carboxylic acid (6.60 g, 29.1 mmol) in THF (150 ml) was treated with borane/THF (87 ml of a 1M solution). The mixture was refluxed for 6 hr, then powdered iron (16.3 g, 291 mmol) was added, followed by acetic acid ( 150 ml). Reflux was maintained for 6 hr, the mixture was filtered, evaporated and partitioned (AcOEt/aqueous $NaHCO_3$-solution). The organic phase was dried ($Na_2SO_4$), concentrated and chromatographed ($SiO_2$ with $CH_2Cl/MeOH=93/7$) to provide 2.0 g (34%) of the title compound as a white solid material. Mp. 144–145° C. (AcOEt), MS: m/e=202 ($M^+$).

c) [4-Amino-6-(3,4-dihydro-naphthalen-2-yl)-pyridin-2-yl]-methanol 1:1 fumarate

Following the general method described in example 19b, the title compound was obtained as an off-white crystalline material by reaction of (4-amino-6-bromo-pyridin-2-yl)-methanol with palladium tetrakis(triphenylphosphine), 3,4-dihydro-naphthalene-2-boronic acid (example 19a) and aqueous 2M $K_2CO_3$ and crystallization of the free base as the fumarate salt. Mp. 113° C. (dec) (MeOH/$Et_2O$), MS: m/e=252 ($M^+$).

EXAMPLE 24

2-(3,4-Dihydro-naphthalen-2-yl)-5-methyl-pyridin-4-yl-amine fumarate

Following the general method described in example 19b, the title compound was obtained as an off-white crystalline material by reaction of 2-bromo-5-methyl-pyridin-4-ylamine (A. Puszko, Z. Talik, Pol. Pr. Nauk. Akad. Ekon. Im. Oskara Langego Wroclawiu, 1980, 167, 177) with palladium tetrakis(triphenylphosphine), 3,4-dihydro-naphthalene-2-boronic acid (example 19a) and aqueous 2M $K_2CO_3$ and crystallization of the free base as the fumarate salt. Mp.>200° C. dec. (MeOH), MS: m/e=236 ($M^+$).

EXAMPLE 25

2-(3,4-Dihydro-naphthalen-2-yl)-3-methyl-pyridin-4-yl-amine

Following the general method described in example 19b, the title compound was obtained as a dark grey crystalline material by reaction of 2-bromo-3-methyl-pyridin-4-ylamine (A. Puszko, Z. Talik, Pol. Pr. Nauk. Akad. Ekon. Im. Oskara Langego Wroclawiu, 1980, 167, 177) with palladium tetrakis(triphenylphosphine), 3,4-dihydro-naphthalene-2-boronic acid (example 19a) and aqueous 2M $K_2CO_3$. Mp. 87–88° C. (MeOH), MS: m/e=236 ($M^+$).

EXAMPLE 26

2-(3,4-Dihydro-naphthalen-2-yl)-6-methyl-pyridin-4-yl-amine fumarate a) 2-Bromo-6-ethyl-pyridine 1-oxide To a solution of 2-bromo-6-ethyl-pyridine (15.4 g, 82.8 mmol) (S. G. Davies and M. R. Shipton, J. Chem. Soc., Perkin Trans. 1, 1991, 3, 501) in acetic acid (15 ml) peracetic acid (26 ml of a 39%) solution) was added maintaining T<50° C. After completed addition the mixture was stirred at 50° C. for 5 hr and then cooled to rt. Crushed ice (40 g) was added and the mixture was made basic (pH 12) using 40% KOH solution. After extraction with $CHCl_3$ (6×60 ml) the combined organic phases were dried ($Na_2CO_3$) and evaporated to give 20.0 g (>100%) of the title compound, MS: m/e=201 ($M^+$) as a yellow oil.

b) 2-Bromo-6-ethyl-4-nitro-pyridine 1-oxide

With ice bath cooling $HNO_3$ (100%, 25 ml) was added dropwise to 2-bromo-6-ethyl-pyridine 1-oxide (20.0 g, 99 mmol), followed by $H_2SO_4$ (98%, 17 ml). The mixture was stirred at 90° C. for 90 min and then cooled to rt. Crushed ice (500 g) was added and the mixture was made basic (pH 12) using 28% NaOH solution. After extraction with AcOEt (4×250 ml) the combined organic phases were dried ($Na_2CO_3$) and evaporated to give 15.9 g (65%) of a yellow Solid mass which was directly used in the next step c) 2-Bromo-6-methyl-pyridin-4-yl-amine A solution of 2-bromo-6-ethyl-4-nitro-pyridine 1-oxide (15.9 g, 69 mmol) in acetic acid (310 ml) was treated with powdered iron (25.8 g, 462 mmol). The mixture was slowly heated to 100° C. and kept for 1 hr. Then the reaction mixture was cooled to rt and filtered. After evaporation of the solvent the residue was crystallized to yield the title compound as a beige material (88%). Mp. 75–77° C. (pentane), MS: m/e=200 ($M^+$).

d) 2-(3,4-Dihydro-naphthalen-2-yl)-6-methyl-pyridin-4-yl-amine 1:1 fumarate

Following the general method described in example 19b, the title compound was obtained as a beige crystalline material by reaction of 2-bromo-6-methyl-pyridin-4-yl-amine with palladium tetrakis(triphenylphosphine), 3,4-dihydro-naphthalene-2-boronic acid (example 19a) and aqueous 2M $K_2CO_3$ and crystallization of the free base as the fumarate salt. Mp.>230° C. dec. (MeOH), MS: m/e=250 ($M^+$).

EXAMPLE 27

[2-(3,4-Dihydro-naphthalen-2-yl)-pyridin-4-yl]-methyl-amine fumarate a) [2-(3,4-Dihydro-naphthalen-2-yl)-pyridin-4-yl]-carbamic acid ethyl ester A solution of 2-(3,4-dihydro-naphthalen-2-yl)-pyridin-4-yl-amine (0.80 g, 3.6 mmol) in pyridine (20 ml) was cooled to 0° C. and ethylchloroformate (0.47 g, 4.3 mmol) was slowly added. Stirring was continued for 72 hr. Then the solvent was evaporated and the residue was partitioned (AcOEt /$H_2O$). The organic phase was dried ($MgSO_4$), concentrated and chromatographed ($SiO_2$ with $CH_2Cl_2$/ $CH_3OH$=98/2) to give the title compound (0.36 g, 36%) as a yellow oil. MS: m/e=294 ($M^+$).

b) [2-(3,4-Dihydro-naphthalen-2-yl)-pyridin-4-yl]-methyl-amine 1:1 fumarate

A solution of N-[2-(3,4-dihydro-naphthalen-2-yl)-pyridin-4-yl]-oxalamic acid ethyl ester (0.36 g, 1.2 mmol) in THF (20 ml) was slowly added to an ice bath cooled mixture of lithium aluminum hydride (0.10 g , 2.6 mmol) in THF (20 ml). The resulting mixture was refluxed for 30 min, quenched with aqueous saturated Seignette-salt solution and extracted with AcOEt. The organic phase was dried over $Na_2SO_4$, concentrated and chromatographed ($SiO_2$ with $CH_2Cl_2/CH_3OH/NH_4OH$=140/10/1) to give [2-(3,4-dihydro-naphthalen-2-yl)-pyridin-4-yl]-methyl-amine as a yellow oil (0.12 g, 42%) which was crystallized as the white fumarate salt. Mp. 106–107° C. (MeOH/$Et_2O$), MS: m/e= 236 ($M^+$).

EXAMPLE 28

C-[6-(3,4-Dihydro-naphthalen-2-yl)-pyridin-2-yl]-methylamine hydrochloride a) 2-(6-Bromo-pyridin-2-yl-methyl)-isoindole-1,3-dione A solution of (6-bromo-pyridin-2-yl)-methanol (3.37 g, 17.9 mmol) (H. Tsukube et al., J. Org. Chem., 1993, 58, 4389), triphenylphosphine (5.17 g, 19.7 mmol) and phtalimide (2.90 g, 19.7 mmol) in THF was cooled in an ice bath. A solution of diethylazodicarboxylate (3.43 g, 19.7 mmol) in THF (15 ml) was added slowly and the mixture was left to reach rt. Stirring was continued for 17 hr, then the solvent was distilled off and the residue chromatographed ($SiO_2$ with hexane/AcOEt=4/1) to provide 3.42 g (66%) of the title compound as a colorless viscous oil. MS: m/e=316 ($M+H^+$).

b) 2-[6-(3,4-Dihydro-naphthalen-2-yl)-pyridin-2-yl-methyl]-isoindole-1,3-dione

Following the general method described in example 19b, the title compound was obtained as a white crystalline material by reaction of 2-(6-bromo-pyridin-2-yl-methyl)-isoindole-1,3-dione with palladium tetrakis (triphenylphosphine), 3,4-dihydro-naphthalene-2-boronic acid (example 19a) and aqueous 2M $K_2CO_3$. MS: m/e=366 ($M^+$).

c) C-[6-(3,4-Dihydro-naphthalen-2-yl)-pyridin-2-yl]-methylamine 1:1 hydrochloride A solution of 2-[6-(3,4-dihydro-naphthalen-2-yl)-pyridin-2-yl-methyl]-isoindole-1,3-dione (0.88 g, 2.4 mmol) in ethanol (25 ml) was treated with hydrazine hydrate (0.36 g, 7.2 mmol) and refluxed for 2 hr. The cooled mixture was filtered, concentrated and chromatographed ($SiO_2$ with $CH_2Cl_2/CH_3OH/NH_4OH$=140/10/1) to give the free base of the title compound as a colorless oil (0.45 g, 79%) which was crystallized as the white hydrochloride salt. Mp. 203–204° C. (MeOH/$Et_2O$), MS: m/e=236 ($M^+$).

EXAMPLE 29

2- (6,7-Dihydro-benzo[b]thiophen-5-yl )-pyridin-4-yl-amine fumarate a) 5-Bromo-6,7-dihydro-benzo[b]thiophene In analogy to the synthesis of 3-bromo-1,2-dihydro-naphthalene (referred to in example 19a) a cooled (10° C.) solution of 6,7-dihydro-5H-benzo[b]thiophen-4-one (10 g, 65.7 mmol) in ether (100 ml) was treated dropwise with bromine (3.5 ml, 65.7 mmol). After 1 hr the reaction mixture was successively extracted with ice water (twice) and saturated aqueous $NaHCO_3$. The organic phase was dried ($Na_2SO_4$), concentrated and directly used in the next step.

The bromoketone was dissolved in a mixture of THF (115 ml) and EtOH (115 ml). Sodium borohydride (1.9 g, 50 mmol) was added and the mixture was stirred for 90 min at rt. After addition of aqueous HCl (1N, 90 ml) all volatiles were evaporated. The oily residue was partitioned (toluene/H$_2$O=125 ml: 50 ml) and the organic phase directly used in the next step.

To the solution of the bromoalkohol in toluene was added p-toluenesulfonic acid (0.65 g, 3.5 mmol) and the mixture was refluxed for 15 hr. Then aqueous NaOH (1N, 65 ml) was added, and the organic phase was dried (MgSO$_4$), concentrated and chromatographed (SiO$_2$ with hexane) to provide 3.7 g (26%) of the title compound as a yellow oil. $^1$H-Nmr (250 MHz, CDCl$_3$): δ=2.87 and 2.98 (mc, CH$_2$), 6.74 (s, 1H, CH=CBr), 6.75–6.82 (m, 2H, arom-H).

b) 6,7-Dihydro-benzo[b]thiophene-5-boronic acid

Following the general method described in example 19a, 5-bromo-6,7-dihydro-benzo[b]thiophene was reacted with tert.-butyllithium solution followed by triisopropylborate and 3N HCl. The title compound was obtained as a white crystalline material after chromatography (SiO$_2$ with CH$_2$Cl$_2$-MeOH=98:2). MS: m/e=179 (M–H$^-$).

c) 2-(6,7-Dihydro-benzo[b]thiophen-5-yl)-pyridin-4-yl-amine 1:1 fumarate

Following the general method described in example 19b, the title compound was obtained as a white crystalline material by reaction of 2-bromo-pyridin-4-yl-amine with palladium tetrakis(triphenylphosphine), 6,7-dihydro-benzo[b]thiophene-5-boronic acid and aqueous 2M K$_2$CO$_3$ solution and crystallization of the free base as the fumarate salt. Mp. 199–200° C. (MeOH), MS: m/e=228 (M$^+$).

EXAMPLE 30

2-(7-Chloro-3,4-dihydro-naphthalen-2-yl)-pyridin-4-ylamine fumarate a) 3-Bromo-6-chloro-1,2-dihydro-naphthalene Following the general method described in example 29a, the title compound was obtained as a colorless oil by reaction of 7-chloro-1-tetralone with bromine, sodium borohydride and p-toluenesulfonic acid. $^1$H-Nmr (250 MHz, CDCl$_3$): δ=2.76 and 2.86 (mc, CH$_2$), 6.73 (s, 1H, CH=CBr), 6.95 (d, J=2 Hz, 1H, arom-H), 7.01 (d, J=8 Hz, 1H, arom-H), 7.10 (dd, J=8 Hz, J=2 Hz, 1H, arom-H).

b) -Chloro-3,4-dihydro-naphthalene-2-boronic acid

Following the general method described in example 19a, the title compound was obtained as a white crystalline material by reaction of 3-bromo-6-chloro-1,2-dihydro-naphthalene with tert.-butyllithium solution followed by triisopropylborate and 3N HCl. Mp. 151–152° C. (pentane), MS: m/e=207 (M–H$^-$).

c) 2-(7-Chloro-3,4-dihydro-naphthalen-2-yl)-pyridin-4-yl-amine 1:1 fumarate

Following the general method described in example 19b, the title compound was obtained as a white crystalline material by reaction of 2-bromo-pyridin-4-ylamine with palladium tetrakis(triphenylphosphine), 7-chloro-3,4-dihydro-naphthalene-2-boronic acid and aqueous 2M K$_2$CO$_3$ solution and crystallization of the free base as the fumarate salt. Mp. 205–207° C. (MeOH), MS: m/e=250 (M$^+$).

EXAMPLE 31

2-(5-Methoxy-3,4-dihydro-naphthalen-2-yl)-pyridin-4-yl-amine fumarate a) -Bromo-8-methoxy-1,2-dihydro-naphthalene Following the general method described in example 29a, the title compound was obtained as a colorless oil by reaction of 5-methoxy-1-tetralone with bromine, sodium borohydride and p-toluenesulfonic acid. $^1$H-Nmr (250 MHz, CDCl$_3$): δ=2.74 and 2.94 (mc, CH$_2$), 3.82 (s, 3H, OCH$_3$), 6.62 (d, J=8 Hz, 1H, arom-H), 6.75 (s, 1H, CH=CBr), 6.76 (d, J=8 Hz, 1H, arom-H), 7.11 (t, J=8 Hz, 1H, arom-H).

b) -Methoxy-3,4-dihydro-naphthalene-2-boronic acid

Following the general method described in example 19a, the title compound was obtained as a white crystalline material by reaction of 3-bromo-8-methoxy-1,2-dihydro-naphthalene with tert.-butyllithium solution followed by triisopropylborate and 3N HCl. Mp. 174–175° C. (pentane), MS: m/e=203 (M–H$^-$).

c) 2-(5-Methoxy-3,4-dihydro-naphthalen-2-yl)-pyridin-4-yl-amine 1:1 fumarate

Following the general method described in example 19b, the title compound was obtained as a white crystalline material by reaction of 2-bromo-pyridin-4-ylamine with palladium tetrakis(triphenylphosphine), 5-methoxy-3,4-dihydro-naphthalene-2-boronic acid and aqueous 2M K$_2$CO$_3$ solution and crystallization of the free base as the fumarate salt. Mp. 207–208° C. (MeOH), MS: m/e=252 (M$^-$).

EXAMPLE 32

2-(5,8-Dimethyl-3,4-dihydro-naphthalen-2-yl)-pyridin-4-yl-amine fumarate a) 3-Bromo-5,8-dimethyl-1,2-dihydro-naphthalene Following, the method referred to in example 19a, the title compound was obtained as a colorless oil by reaction of 5,8-dimethyl-1-tetralone with bromine, sodium borohydride and p-toluenesulfonic acid. MS: m/e=236 (M$^+$).

b) 8-Dimethyl-3,4-dihydro-naphthalene-2-boronic acid

Following the general method described in example 29a, the title compound was obtained as a white crystalline material by reaction of 3-bromo-5,8-dimethyl-1,2-dihydro-naphthalene with tert.-butyllithium solution followed by triisopropylborate and 3N HCl. Mp. 163–164° C. (pentane), MS: m/e=261 (M+OAc$^-$).

c) 2-(5,8-Dimethyl-3,4-dihydro-naphthalen-2-yl)-pyridin-4-yl-amine 1:1 fumarate

Following the general method described in example 19b, the title compound was obtained as a white crystalline material by reaction of 2-bromo-pyridin-4-yl-amine with palladium tetrakis(triphenylphosphine), 5,8-dimethyl-3,4-dihydro-naphthalene-2-boronic acid and aqueous 2M K$_2$CO$_3$ solution and crystallization of the free base as the fumarate salt. Mp. 232–233° C. (MeOH), MS: m/e=250 (M$^+$).

EXAMPLE 33

2-(7-Methoxy-3,4-dihydro-naphthalen-2-yl)-pyridin-4-yl-amine fumarate a) 3-Bromo-6-methoxy-1,2-dihydro-naphthalene Following the method referred to in example 29a, the title compound was obtained as a colorless oil by reaction of 7-methoxy-1-tetralone with bromine, sodium borohydride and p-toluenesulfonic acid. $^1$H-Nmr (250 MHz, CDCl$_3$): δ2.76 and 2.86 (mc, CH$_2$), 3.76 (s, CH$_3$), 6.54 (d, J=3 Hz, 1H, arom-H), 6.68 (dd, J=8 Hz, J=3 Hz, 1H, arom-H), 6.75 (s, 1H, CH=CBr), 7.00 (d, J=8 Hz, 1H, arom-H).

b) 7-Methoxy-3,4-dihydro-naphthalene-2-boronic acid

Following the general method described in example 19a, the title compound was obtained as a white solid material by reaction of 3-bromo-6-methoxy-1,2-dihydro-naphthalene with tert.-butyllithium solution followed by triisopropylborate and 3N HCl. MS: m/e=263 (M+OAc$^-$).

c) 2-(7-Methoxy-3,4-dihydro-naphthalen-2-yl)-pyridin-4-yl-amine 1:1 fumarate

Following the general method described in example 19b, the title compound was obtained as a beige crystalline material by reaction of 2-bromo-pyridin-4-yl-amine with palladium tetrakis(triphenylphosphine), 7-methoxy-3,4-dihydro-naphthalene-2-boronic acid and aqueous 2M $K_2CO_3$ solution and crystallization of the free base as the fumarate salt. Mp. 193–194° C. (MeOH/$Et_2O$), MS: m/e=252 ($M^+$).

EXAMPLE 34

2-(5,7-Dimethyl-3,4-dihydro-naphthalen-2-yl)-pyridin-4-yl-amine fumarate a) 3-Bromo-6,8-dimethyl-1,2-dihydro-naphthalene Following the method referred to in example 29a, the title compound was obtained as a colorless oil by reaction of 5,7-dimethyl-1-tetralone with bromine, sodium borohydride and p-toluenesulfonic acid. MS: m/e=236 ($M^+$).

b) 5,7-Dimethyl-3,4-dihydro-naphthalene-2-boronic acid

Following the general method described in example 19a, the title compound was obtained as a white solid material by reaction of 3-bromo-6,8-dimethyl-1,2-dihydro-naphthalene with tert.-butyllithium solution followed by triisopropylborate and 3N HCl. MS: m/e=261 (M+$OAc^-$).

c) 2-(5,7-Dimethyl-3,4-dihydro-naphthalen-2-yl)-pyridin-4-yl-amine 1:1 fumarate

Following, the general method described in example 19b, the title compound was obtained as a white crystalline material by reaction of 2-bromo-pyridin-4-yl-amine with palladium tetrakis(triphenylphosphine), 5,7-dimethyl-3,4-dihydro-naphthalene-2-boronic acid and aqueous 2M $K_2CO_3$ solution and crystallization of the free base as the fumarate salt. Mp. 231–232° C. (MeOH), MS: m/e:=250 ($M^+$).

EXAMPLE 35 rac.-2-(4-Methyl-3,4-dihydro-naphthalen-2-yl)-pyridin-4-yl-amine fumarate a) rac.-3-Bromo-1-methyl-1,2-dihydro-naphthalene Following the method referred to in example 29a, the title compound was obtained as a colorless oil by reaction of 4-methyl-1-tetralone with bromine, sodium borohydride and p-toluenesulfonic acid. MS: m/e=222 ($M^+$).

b) rac.-4-Methyl-3,4-dihydro-naphthalene-2-boronic acid

Following the general method described in example 19a, the title compound was obtained as a white crystalline material by reaction of rac.-3-bromo-1-methyl-1,2-dihydro-naphthalene with tert.-butyllithium solution followed by triisopropylborate and 3N HCl. MS: m/e=187 (M–$H^-$).

c) rac.-2-(4-Methyl-3,4-dihydro-naphthalen-2-yl)-pyridin-4-yl-amine 1:1 fumarate Following the general method described in example 19b, the title compound was obtained as a white crystalline material by reaction of 2-bromo-pyridin-4-yl-amine with palladium tetrakis(triphenylphosphine), rac.-4-methyl-3,4-dihydro-naphthalene-2-boronic acid and aqueous 2M $K_2CO_3$ solution and crystallization of the free base as the fumarate salt. Mp. 176–177° C. (MeOH/$Et_2O$), MS: m/e=237 ($M+H^+$).

EXAMPLE 36

2-(7-Chloro-3,4-dihydro-naphthalen-2-yl)-6-methyl-pyridin-4-yl-amine fumarate

Following the general method described in example 19, the title compound was obtained as a white crystalline material by reaction of 2-bromo-6-methyl-pyridin-4-ylamine (cf example 26c) with palladium tetrakis(triphenylphosphine), 7-chloro-3,4-dihydro-naphthalene-2-boronic acid (cf example 30b) and aqueous 2M $K_2CO_3$ and crystallization of the free base as the fumarate salt. Mp. 232–233° C. (MeOH), MS: m/e=285 ($M+H^+$).

EXAMPLE 37

2-(7-Chloro-3,4-dihydro-naphthalen-2-yl)-6-methyl-pyridin-4-yl-amine fumarate

Following the general method described in example 19b, the title compound was obtained as a white crystalline material by reaction of 2-bromo-6-methyl-pyridin-4-ylamine (cf example 22) with palladium tetrakis(triphenylphosphine), 7-chloro-3,4-dihydro-naphthalene-2-boronic acid (cf example 30b) and aqueous 2M $K_2CO_3$ and crystallization of the free base as the fumarate salt. Mp. 232–233° C. (MeOH), MS: m/e=271 ($M+H^+$).

EXAMPLE 38 rac.-2-Methyl-6-(4-methyl-3,4-dihydro-naphthalen-2-yl)-pyridin-4-yl-amine fumarate Following the general method described in example 19b, the title compound was obtained as an off-white crystalline material by reaction of 2-bromo-6-methyl-pyridin-4-yl-amine (cf example 22) with palladium tetrakis(triphenylphosphine), rac.-4-methyl-3,4-dihydro-naphthalene-2-boronic acid (cf example 35b) and aqueous 2M $K_2CO_3$ and crystallization of the free base as the fumarate salt. Mp. 183–185° C. dec. (MeOH), MS: m/e=250 ($M^+$).

EXAMPLE 39

2-(7-Chloro-3,4-dihydro-naphthalen-2-yl)-5-methyl-pyridin-4-yl-amine fumarate

Following, the general method described in example 19b, the title compound was obtained as a white crystalline material by reaction of 2-bromo-5-methyl-pyridin-4-yl-amine (cf example 24) with palladium tetrakis(triphenylphosphine), 7-chloro-3,4-dihydro-naphthalene-2-boronic acid (cf example 30b) and aqueous 2M $K_2CO_3$ and crystallization of the free base as the fumarate salt. Mp.>250° C. (MeOH), MS: m/e=271 ($M+H^+$).

EXAMPLE 40 rac.-5-Methyl-2-(4-methyl-3,4-dihydro-naphthalen-2-yl)-pyridin-4-yl-amine fumarate Following the general method described in example 19b, the title compound, was obtained as a white crystalline material by reaction of 2-bromo-5-methyl-pyridin-4-yl-amine (cf example 24) with palladium tetrakis(triphenylphosphine), rac.-4-methyl-3,4-dihydro-naphthalene-2-boronic acid (example 35b) and aqueous 2M $K_2CO_3$ and crystallization of the free base as the fumarate salt. Mp. 210–211° C. (MeOH), MS: m/e=251 ($M+H^+$).

EXAMPLE 41

2-(6,7-Dihydro-benzo[b]thiophen-5-yl)-5-methyl-pyridin-4-yl-amine fumarate

Following the general method described in example 19b, the title compound was obtained as a light yellow crystalline material by reaction of 2-bromo-5-methyl-pyridin-4-ylamine (cf example 24) with palladium tetrakis (triphenylphosphine), 6,7-dihydro-benzo[b]thiophene-5-boronic acid (cf example 29b) and 2M $K_2CO_3$ and crystallization of the free base as the fumarate salt. Mp. 218–219° C. (MeOH), MS: m/e=243 (M+H$^+$).

Example A

Tablet Formulation (Wet Granulation)

| | | mg/tablet | | | |
|---|---|---|---|---|---|
| Item | Ingredients | 5 mg | 25 mg | 100 mg | 500 mg |
| 1. | Active Ingredient* | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

*A compound of formula 1A, 1B or a combination thereof or a pharmaceutically acceptable salt thereof.

Manufacturing Procedure

1. Mix items 1, 2, 3 and 4 and granulate with purified water.

2. Dry the granulation at 50° C.

3. Pass the granulation through suitable milling equipment.

4. Add item 5 and mix for three minutes; compress on a suitable press.

Example B

Capsule Formulation

| | | mg/tablet | | | |
|---|---|---|---|---|---|
| Item | Ingredients | 5 mg | 25 mg | 100 mg | 500 mg |
| 1. | Active Ingredient | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2, and 3 in a suitable mixer for 30 minutes.

2. Add items 4 and 5 and mix for 3 minutes.

3. Fill into a suitable capsule.

4. Add item 5 and mix for three minutes; compress on a suitable press.

What is claimed is:
1. A compound of formula

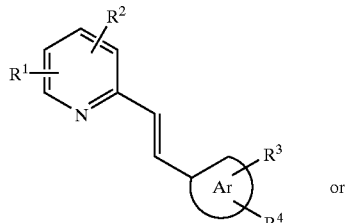

IA

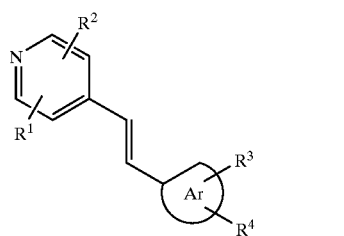

IB wherein
one of $R^1$ and $R^2$ is —$(CH_2)_n NR^5 R^{5'}$ and the other of $R^1$ and $R^2$ is selected from the group hydrogen, alkyl, —$(CH_2)_n NR^5 R^{5'}$ and —$(CH_2)_{n+1} OH$;

$R^5$ and $R^{5'}$ are each independently hydrogen;

$R^3$ and $R^4$ are each independently selected from the group hydrogen, lower alkyl lower alkoxy, halogen, trifluoromethyl and hydroxy;

Ar is selected from the group phenyl and thiophenyl;

n is 0;

or a pharmaceutically acceptable acid addition salt thereof, with the proviso that when Ar is unsubstituted phenyl and one of $R^1$ and $R^2$ is H, the other is not 2-amino or 5-amino and with the exception of 3-amino-2-[4-hydroxystyryl]pyridine and 3-amino-2-styryl-6-pyridinylamine.

2. A compound of formula

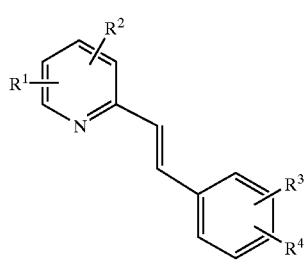

IA-1 wherein one of $R^1$ and $R^2$ is —$(CH_2)_n NR^5 R^{5'}$ and the other of $R^1$ and $R^2$ is selected from the group hydrogen, alkyl, —$(CH_2)_n NR^5 R^{5'}$ and —$(CH_2)_{n+1} OH$;

$R^5$ and $R^{5'}$ are each independently hydrogen; and $R^3$ and $R^4$ are each independently selected from the group of hydrogen, lower alkyl, lower alkoxy, halogen, trifluoromethyl and hydroxy; and n=0;

or a pharmaceutically acceptable acid addition salt thereof, with the proviso that when the phenyl group is unsubstituted and one of $R^1$ and $R^2$ is H, the other is not 2-amino or 5-amino and with the exception of 3-amino- 2-[4-hydroxystyryl]pyridine and 3-amino-2-styryl-6-pyridinylamine.

3. A compound of formula IA-1 according to claim 2, selected from the group
trans-4-methyl-2-styryl-6-pyridinyl-amine and trans-2-styryl-4-pyridinyl-amine.

4. A pharmaceutical composition comprising a compound of formula IA,

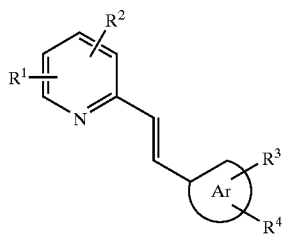

IA wherein
one of $R^1$ and $R^2$ is —$(CH_2)_nNR^5R^{5'}$ and the other of $R^1$ and $R^2$ is selected from the group hydrogen, alkyl, —$(CH_2)_nNR^5R^{5'}$ and —$(CH_2)_{n+1}OH$;
$R^5$ and $R^{5'}$ are each independently hydrogen;
$R^3$ and $R^4$ are each independently selected from the group hydrogen, lower alkyl, lower alkoxy, halogen, trifluoromethyl and hydroxy;
Ar is selected from the group phenyl and thiophenyl;
n is 0;
or a pharmaceutically acceptable acid addition salt thereof, with the proviso that when Ar is unsubstituted phenyl and one of $R^1$ and $R^2$ is H, the other is not 2-amino or 5-amino and with the exception of 3-amino-2-[4-hydroxystyryl]pyridine and 3-amino-2-styryl-6-pyridinylamine;
combinations thereof or a pharmaceutically acceptable salt thereof and a pharmaceutically acceptable carrier.

5. A process for preparing a compound of formula IA-1a comprising
a) reacting a compound of formula

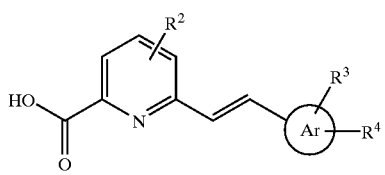

IIA with diphenyl phosphoryl azide, forming a compound of formula

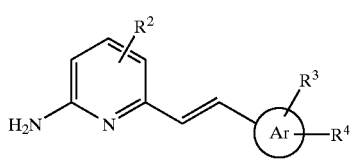

IA-1a wherein
$R^2$ is selected from the group hydrogen, lower alkyl, —$(CH_2)_nNR^5R^{5'}$ and —$(CH_2)_{n+1}OH$;

$R^5$ and $R^{5'}$ are each independently hydrogen; and
$R^3$ and $R^4$ are each independently selected from the group hydrogen, lower alkyl, lower alkoxy, halogen, trifluoromethyl and hydroxy;
Ar is selected from the group phenyl and thiophenyl and
n is 0.

6. A method of treating Alzheimer's disease, Parkinson's disease, Huntington's disease, ALS (amyotrophic lateral sclerosis), neurodegeneration associated with bacterial or viral infections, depression, or chronic or acute pain comprising administering a therapeutically effective amount of a compound of formulae IA,

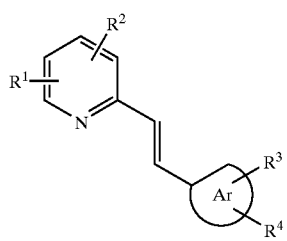

IA wherein
one of $R^1$ and $R^2$ is —$(CH_2)_nNR^5R^{5'}$ and the other of $R^1$ and $R^2$ is selected from the group hydrogen, alkyl, —$(CH_2)_nNR^5R^{5'}$ and —$(CH_2)_{n+1}OH$;
$R^5$ and $R^{5'}$ are each independently hydrogen;
$R^3$ and $R^4$ are each independently selected from the group hydrogen, lower alkyl, lower alkoxy, halogen, trifluoromethyl and hydroxy;
Ar is selected from the group phenyl and thiophenyl; and
n is 0;
or a pharmaceutically acceptable acid addition salt thereof, with the proviso that when Ar is unsubstituted phenyl and one of $R^1$ and $R^2$ is H, the other is not 2-amino or 5-amino and with the exception of 3-amino-2-[4-hydroxystyryl]pyridine and 3-amino-2-styryl-6-pyridinylamine;
combinations thereof or a pharmaceutically acceptable salt thereof to a patient in need of such treatment.

7. A method of treating Alzheimer's disease in accordance with claim 6.

8. A method of treating Parkinson's disease in accordance with claim 6.

9. A method of treating, Huntington's disease in accordance with claim 6.

10. A method of treating, ALS (amyotrophic lateral sclerosis) in accordance with claim 6.

11. A method of treating neurodegeneration associated with bacterial or viral infections in accordance with claim 6.

12. A method of treating depression in accordance with claim 6.

13. A method of treating chronic or acute pain in accordance with claim 6.

* * * * *

UNITED STATES PATENT AND TRADEMARK OFFICE
CERTIFICATE OF CORRECTION

PATENT NO. : 6,951,875 B2
APPLICATION NO. : 10/277002
DATED : October 4, 2005
INVENTOR(S) : Alanine et al.

Page 1 of 1

It is certified that error appears in the above-identified patent and that said Letters Patent is hereby corrected as shown below:

IN THE CLAIMS

• Claim 1, Column 30, lines 5-20: the word "or" and formula IB should be omitted.
• Claim 1, Column 30, line 27: "alkyl" should read -- lower alkyl -- .
• Claim 1, Column 30, lines 39-41: "2-amino or 5-amino and with the exception of 3-amino-2-[4-hydroxystyryl]pyridine and 3-amino-2-styryl-6-pyridinylamine." Should read -- 3-amino or 6-amino, where the position at which the arylethenyl group is attached is noted as 2-, and also with the exception of 2-(4-hydroxystyryl)pyridine-3-amine and 6-methyl-2-styryl-pyridine-3-amine. -- .
• Claim 2, Column 30, line 56: "alkyl" should read -- lower alkyl -- .
• Claim 2, Column 30, line 67 and Column 31, lines 1 and 2: "2-amino or 5-amino and with the exception of 3-amino-2-[4-hydroxystyryl]pyridine and 3-amino-2-styryl-6-pyridinylamine." Should read -- 3-amino or 6-amino, where the position at which the styryl group is attached is noted as 2-, and with the exception of 2-(4-hydroxystyryl) pyridine-3-amine and 6-methyl-2-styryl-pyridine-3-amine. -- .
• Claim 4, Column 31, line 23; "alkyl" should read -- lower alkyl -- .
• Claim 4, Column 31, lines 34-36: "2-amino or 5-amino and with the exception of 3-amino-2-[4-hydroxystyryl]pyridine and 3-amino-2-styryl-6-pyridinylamine;" Should read -- 3-amino or 6-amino, where the position at which the arylethenyl group is attached is noted as 2-, and with the exception of 2-(4-hydroxystyryl)pyridine-3-amine and 6-methyl-2-styryl-pyridine-3-amine. -- .
• Claim 6, Column 32, line 29: "alkyl" should rend -- lower alkyl -- .
• Claim 6, Column 32, lines 42-44: "2-amino or 5-amino and with the exception of 3-amino-2-[4-hydroxystyryl]pyridine and 3-amino-2-styryl-6-pyridinylamine;" Should read -- 3-amino or 6-amino, where the position at which the arylethenyl group is attached is noted as 2-, and with the exception of 2-(4-hydroxystyryl)pyridine-3-amine and 6-methyl-2-styryl-pyridine-3-amine; -- .

Signed and Sealed this

Sixteenth Day of January, 2007

JON W. DUDAS
*Director of the United States Patent and Trademark Office*